United States Patent
Regensburger et al.

(10) Patent No.: US 12,183,009 B2
(45) Date of Patent: Dec. 31, 2024

(54) IMAGING METHOD AND IMAGING APPARATUS

(71) Applicant: Siemens Healthcare GmbH, Erlangen (DE)

(72) Inventors: Alois Regensburger, Poxdorf (DE); Patrick Wohlfahrt, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 0 days.

(21) Appl. No.: 18/369,149

(22) Filed: Sep. 16, 2023

(65) Prior Publication Data

US 2024/0104740 A1 Mar. 28, 2024

(30) Foreign Application Priority Data

Sep. 23, 2022 (DE) ...................... 10 2022 210 078.6

(51) Int. Cl.
*G06T 7/00* (2017.01)
*A61B 6/00* (2006.01)
(Continued)

(52) U.S. Cl.
CPC ............ *G06T 7/0016* (2013.01); *A61B 6/481* (2013.01); *A61B 6/504* (2013.01); *G06T 5/50* (2013.01);
(Continued)

(58) Field of Classification Search
CPC ......... A61B 6/481; A61B 6/504; A61B 6/486; A61B 8/481; G06T 2207/10116;
(Continued)

(56) References Cited

U.S. PATENT DOCUMENTS

2008/0294038 A1* 11/2008 Weese .................... A61B 6/507
600/431
2010/0254509 A1* 10/2010 Sugaya .................. A61B 6/032
378/16
(Continued)

FOREIGN PATENT DOCUMENTS

DE 102019220147 A1 6/2021
DE 102021200364 A1 7/2022
JP 2008073301 A 4/2008

OTHER PUBLICATIONS

Lesage David et al., A Review of 3D Vessel Lumen Segmentation Techniques: Models, Features and Extraction Schemes; in: Medical Image Analysis 13(6); 2009; pp. 819-845. (28 pages).

*Primary Examiner* — Li Liu
(74) *Attorney, Agent, or Firm* — Lempia Summerfield Katz LLC

(57) ABSTRACT

In an imaging method, a first image is generated at a first capture time by an imaging apparatus, the first image representing part of an object to be depicted. A second image is generated at a second capture time after the first capture time, the second image representing the part of the object to be depicted. A further first image is generated based on the first image using a predefined model relating to a development over time of a contrast agent present in the object to be depicted when generating the first image, the further first image taking into account development over time of the contrast agent from the first capture time to the second capture time. A further second image is generated as a function of the second image and further first image, wherein an effect of the contrast agent on the second image is at least partially compensated.

12 Claims, 3 Drawing Sheets

(51) Int. Cl.
*A61B 6/50* (2024.01)
*G06T 5/50* (2006.01)
*G06T 7/11* (2017.01)
*G06T 7/33* (2017.01)

(52) U.S. Cl.
CPC .................. *G06T 7/11* (2017.01); *G06T 7/33* (2017.01); *G06T 2207/10116* (2013.01); *G06T 2207/20224* (2013.01); *G06T 2207/30101* (2013.01)

(58) Field of Classification Search
CPC ......... G06T 7/0016; G06T 2207/20224; G06T 2207/30101; G06T 2207/30104; G06T 5/50; G06T 2207/10016; G06T 7/11
See application file for complete search history.

(56) References Cited

U.S. PATENT DOCUMENTS

| | | | |
|---|---|---|---|
| 2019/0057506 A1* | 2/2019 | Long | G06T 7/0016 |
| 2019/0154822 A1* | 5/2019 | Berlin | A61B 8/06 |
| 2020/0226801 A1* | 7/2020 | Kaethner | A61B 6/4014 |
| 2021/0192739 A1 | 6/2021 | Tashenov | |
| 2022/0230285 A1 | 7/2022 | Böhm | |

* cited by examiner

IMAGING METHOD AND IMAGING APPARATUS

The present patent document claims the benefit of German Patent Application No. 10 2022 210 078.6, filed Sep. 23, 2022, which is hereby incorporated by reference in its entirety.

TECHNICAL FIELD

The present disclosure relates to an imaging method, wherein a first image is generated at a first capture time by an imaging apparatus, wherein the first image represents part of an object to be depicted, and a second image is generated at a second capture time after the first capture time, wherein the second image represents the part of the object to be depicted. The disclosure is further directed toward a corresponding imaging apparatus and to a computer program product.

BACKGROUND

Contrast agents may be used in imaging methods, in particular in medical imaging methods, for instance using X-ray radiation or other ionizing radiation, to highlight structures, such as vessel structures, in the object to be depicted that otherwise may not be identified in the corresponding image or may not be clearly identified. It is possible that the contrast agent is added at different instants. It is also possible for these additions to be different types of contrast agent or also the same contrast agent. The situation may therefore occur where contrast agent residues from earlier administrations are still present when generating an image after the administration of one particular contrast agent, and this may result in undesirable highlighting of further structures in the image.

In subtraction angiography, two different images of an object to be depicted are captured one after the other, with one image nominally being generated without administration of contrast agent, and thereafter an image with administration of contrast agent. The two images are registered relative to each other and subtracted from one another. In certain examples, only those structures, (e.g., vascular structures to be highlighted by the administration of contrast agent), may be seen in the resulting subtraction image. Contrast agent residues may be undesirably present here, (e.g., image generated first, also referred to as a mask image), and this may ultimately result in artifacts in the subtraction image.

It is also known to segment the images generated by the corresponding imaging apparatuses, and to identify different regions in the image therefore, which correspond to different types of structure, (e.g., tissue types, etc.). Powerful image processing or image analysis algorithms are available for this. These algorithms may also identify, in particular, vascular and skeletal structures and regions that are highlighted by contrast agent.

The publication D. Lesage at al: "A review of 3D vessel lumen segmentation techniques: Models, features and extraction schemes", medical image analysis 13 (6), 2009, 819-845 provides, for example, an overview of the corresponding state of the literature on vessel segmentation, in particular with regard to contrast-enhancing 3D imaging modalities.

SUMMARY AND DESCRIPTION

It is an object of the present disclosure to reduce the effect of undesirable contrast agent residues in images of an imaging method.

The scope of the present disclosure is defined solely by the appended claims and is not affected to any degree by the statements within this summary. The present embodiments may obviate one or more of the drawbacks or limitations in the related art.

The disclosure is based on the idea of modifying a first image by taking into account the development over time of a contrast agent, intentionally or undesirably, present in the object to be depicted and to compensate at least partially the effect of the contrast agent in a second image, which was captured after the first image, by taking into account the modified first image.

According to one aspect, an imaging method is disclosed in which a first image is generated at a first capture time by an imaging apparatus, which image represents an object to be depicted. A second image, which represents the object to be depicted, is generated at a second capture time, which is after the first capture time. A further first image is generated on the basis of the first image, in particular by at least one computing unit of the imaging apparatus, using a predefined model relating to a development over time of a contrast agent present in the object to be depicted when generating the first image. The further first image, which may also be referred to as a modified first image, takes into account the development over time of the contrast agent from the first capture time through to the second capture time. A further second image is generated, in particular by the at least one computing unit, as a function of the second image and as a function of the further first image. An effect of the contrast agent on the second image is at least partially compensated in the second image.

An imaging method or imaging may refer to a method with which image data or pictorial representations, in particular two-dimensional and/or three-dimensional image data or representations, of an object to be depicted may be generated. If medical imaging is involved, then the object is a human or animal patient or one or more body part(s), organ(s), or other anatomical structure(s). Imaging methods may also be used for inanimate objects, e.g., for materials analysis. An imaging modality may refer to a device configured to carry out fundamental parts of an imaging method or the entire imaging method. An imaging modality has at least one sensor apparatus for this in order to capture corresponding physical variables used for generating the image data, with the embodiment of the sensor apparatus differing according to the type of imaging. Different types of imaging are based on the use of X-ray radiation, radio nuclides, ultrasound, or magnetic fields. The sensor apparatus accordingly has one or more suitable sensor(s) and optionally one or more corresponding source(s).

The object to be depicted in the imaging method is therefore, for example, part of a body of a patient, in particular one or more organ(s) or parts of one or more organ(s), with the term "organs" also including, in particular, hollow organs, in particular vessels therefore, (e.g., blood vessels or lymphatic vessels).

Depending on the embodiment of the specific imaging method, a certain period of time is necessary for data acquisition, which is required for generating an image. In other embodiments of the imaging method, images may be generated substantially by snapshots. The first and the second capture times may accordingly be respective times or periods of time. In the case of periods of time, the first capture time may be referred to as a first capture period and the second capture time as the second capture period. In this case, the first and the second capture periods are, for example, separate from each other, such that the capture periods do not overlap. The first capture period accordingly begins at a first start time and ends at a first end time and the second capture period begins at a second start time and ends at a second end time. The second start time is, in particular, after the first end time.

The contrast agent present in the object to be depicted when generating the first image may be established in that the contrast agent was intentionally administered for generating the first image, wherein the contrast agent is supplied to the object before or during generation of the first image therefore, in the case of human or animal patients, for example, by way of an injection or oral intake or the like, in order to purposefully highlight particular regions of the object to be depicted in the first image. The contrast agent may also be present as an undesirable contrast agent residue from an earlier imaging procedure when generating the first image, however. The act of administering the contrast agent is not part of the imaging method, however. In other words, when carrying out the imaging method, it is assumed that a contrast agent has been or will be administered accordingly or is present in the object to be depicted for other reasons.

Depending on the type of contrast agent used, this may be subjected to different dynamics over time after administration in the object. In particular, a spatial distribution of the contrast agent in the object may change as a function of time. For example, a contrast agent injected into a vascular structure or an orally administered one may be flushed out of vascular structure over the course of time, for example, due to the corresponding flow of fluid in the vascular structure, (e.g., a blood flow or lymph flow). With some contrast agents, (e.g., microscopic particles, such as gas-filled bubbles or embolization beads), the particles may also decay over the course of time, so the absolute amount of contrast agent may change over time in addition to the local concentration of the contrast agent. Metabolic processes or fluorescence fading may also contribute to the contrast agent being broken down or degraded.

The model relating to the development over time of the contrast agent reflects the behavior of the contrast agent respectively used as a function of time. For example, the model may characterize a time-dependent spatial distribution and/or concentration of the contrast agent. Depending on the time interval of the second capture time from the first capture time, the model may therefore supply information about how the contrast agent is rendered visible in the imaging. The initial spatial distribution of the contrast agent and/or its initial concentration according to the first image and/or the corresponding intensity values in the first image may be specified, (e.g., as input information), to the model for this purpose and using the model the at least one computing unit may predict or estimate the development over time of the distribution and/or concentration or other properties of the contrast agent. The further first image then corresponds to the first image, with it being assumed, however, that the contrast agent has developed in accordance with the time interval between the first and second capture periods.

Apart from properties of the contrast agent, the model may also include properties of the object, for example, about a type of vessel or a material composition or structure of the object. These items of information may be taken into account when generating the first further image.

The time interval may be a time interval between first end time and second start time if the first capture time and the second capture time are corresponding periods of time. Alternatively, other reference times may be used, for example, the time interval between first start time and second start time, etc.

In other words, assuming that the object is completely unchanged between the first capture time and the second capture time, and the model were to be completely exact, the expectation would be for the second image to be identical to the further first image. This may not be the case, however. Apart from the fact that the model may be based on assumptions that do not necessarily exactly apply, the first and the second images may also differ from each other, for example, in further aspects. For example, individual component parts of the object, for instance soft tissue, may move and/or an instrument, such as a catheter or a biopsy needle or the like, may be introduced into the object and/or a further contrast agent may be administered for generating the second image, etc. The further first image may differ from the second image therefore, even assuming that the model completely correctly reproduces the real development over time of the contrast agent.

The first and/or the second image(s) may also be pre-processed images, for example, segmentation algorithms may be carried out on the basis of corresponding raw images in order to generate the first and/or second image(s). If the first image is, for example, a segmented image, the further first image is, for example, thus likewise generated as a segmented image.

In the imaging method, the contrast agent present when generating the first image occurs as an undesirable residue when generating the second image. In particular, this contrast agent is not purposefully used for generating the second image. Accordingly, the effect of the contrast agent is at least partially compensated in the second further image. This may not necessarily apply to a further contrast agent possibly used for generating the second image, however. Unless stated otherwise, the contrast agent present when generating the first image may hereinafter be referred to as the contrast agent and the contrast agent optionally purposefully used for generating the second image may be referred to as the further contrast agent. This does not preclude the contrast agent and the further contrast agent from being the same substance, however.

The effect of the contrast agent may be compensated in different ways. For example, in the further second image it is possible to mark regions which as evidenced by the further first image go back to the presence of the contrast agent, so a user may take this into account when evaluating the further second image. Compensation is therefore achieved in this case, for example, by the provision of the additional items of information in which image regions of the further second image are possibly contrast agent residues of the contrast agent used for generating the first image. Compensation may also take place, however, in such a way that regions in the second image which go back to the presence of the contrast agent are removed from the second image in order to generate the further second image. These regions may be adapted in the further second image, for example, to their respective environment, or be replaced by an image region known from reference photographs.

Compensation may also take place in such a way that the second image is subtracted from the further first image, or vice versa, so regions which go back to the presence of the contrast agent are removed from the second image, whereas other differences between the first and the second image or the further first image and the second image are also retained in the further second image, for instance changes due to the introduction of an instrument or the administration of the further contrast agent. In other words, the further first image may be used, for example, instead of the first image, as the mask image in a subtraction imaging method, in particular a subtraction angiography method.

Undesirable effects of the contrast agent, which were used when generating the first image, may therefore be reduced in the second image or in the further second image by the imaging method. The disclosure therefore makes it possible, in particular, to generate images of the object one after the other at shorter intervals, it being possible to avoid the effect of the respective contrast agent, in particular when offset against subsequent images, for example a subtraction.

The imaging method may be an X-ray based imaging method, in particular, an angiography method.

In different embodiments of the imaging method, the second image depicts the further contrast agent used for generating the second image. As mentioned above for the contrast agent, the act of administering the further contrast agent is not part of the imaging method either.

The second image thus depicts the further contrast agent as well as the undesirable residues of the contrast agent. The effect of the further contrast agent, (e.g., the desired effect of the further contrast agent), on the second image may be analyzed more reliably by the at least partial compensation of the effect of the contrast agent.

According to at least one embodiment, the model relates to a spatial distribution and/or concentration of the contrast agent as a function of time.

The development over time of the contrast agent therefore corresponds to a change over time in the spatial distribution and/or concentration.

According to at least one embodiment of the imaging method, a differential image is generated by subtracting the further first image from the second image or the second image from the further first image. The further second image is generated as a function of the differential image or corresponds to the differential image.

In these embodiments, the imaging method may also be referred to as a subtraction imaging method, therefore. In particular, the above-mentioned dose or administration of the further contrast agent for generating the second image takes place. If vascular structures are highlighted in the second image by the dose of the second contrast agent, then the imaging method is, in particular, a subtraction angiography method.

The disclosure proves to be particularly advantageous here since the principle of subtraction imaging is based on the assumption that no anatomical structures are highlighted by a contrast agent in the corresponding mask image but instead only in the object image photographed later, which is also referred to as a fill image.

In this connection, the contrast agent is undesirable in the first image as well as in the second image. If the first image were to be used as a mask image, the contrast agent would be only inadequately compensated in the resulting differential image since the development over time would not be taken into account.

In further embodiments of the imaging method, further images of the object may also be generated by the imaging apparatus or a further imaging apparatus between generation of the first image and generation of the second image.

According to at least one embodiment, the imaging apparatus is embodied as a method for subtraction imaging, in particular for subtraction angiography. The further first image corresponds to a mask image of subtraction imaging, in particular the further first image is used as a mask image. The second image corresponds to an object image of subtraction imaging, is used, in particular as an object image therefore, with the object image also being referred as a vascular image in the case of subtraction angiography.

In particular, the further contrast agent is administered in such embodiments therefore for generating the second image.

While the mask image shows static structures or background structures, for instance skeletal structures or the like therefore, and undesirable residues of the contrast agent while taking into account the development over time of the contrast agent, it does not show the further contrast agent. The vascular image, by contrast, shows the static structures of the mask image as well as the further contrast agent, for example highlighted vascular structures therefore, and the modified residues of the contrast agent according to the development over time.

The modified undesirable residues of the contrast agent may be compensated in the second image by the use of the further first image and not, for instance, the first image as the mask image.

According to at least one embodiment, the first image is segmented, in particular by the at least one computing unit. The further first image and/or the further second image is/are generated on the basis of the segmented first image.

In particular, different regions are identified in the first image by the segmenting, which regions may be assigned to different types of structure, tissue, or the like.

In order to generate the further first image, for example, regions in the segmented first image, which according to the segmentation correspond to the contrast agent, may be subjected to the development over time according to the model, therefore. For example, static structures of the segmented first image, identified according to the segmentation, may be utilized for image registration for generating the further second image.

According to at least one embodiment, generating the further first image includes modifying a first region of the segmented first image, which represents the contrast agent, as a function of the model according to the development over time of the contrast agent from the first capture time through to the second capture time.

Instead of the first region, which represents the contrast agent, the further first image then includes, in particular, the first region modified according to the model. The model may thus be purposefully applied to regions of the contrast agent whereby the development over time of the contrast agent is more accurate in the further first image. Other regions of the segmented first image, which do not represent the contrast agent, may be modified according to other models, or not be modified at all, in order to generate the further first image.

According to at least one embodiment, the second image is segmented, and a second region is determined in the segmented second image that corresponds to the modified first region of the first image. The second region is removed or partially removed from the segmented second image in order to generate the further second image.

According to at least one embodiment, a further first region of the segmented first image is determined which corresponds to a stationary anatomical structure, also referred to as a static anatomical structure. The second image is segmented and a further second region of the segmented second image is determined which corresponds to the stationary anatomical structure. A transformation for image registration is determined as a function of the further first region and the further second region, in particular by the at least one computing unit. The further second image is generated as a function of the transformation.

For specific applications or application situations, which may arise with the method, and which are not explicitly described here, it may be provided that an error message and/or a request to input a user acknowledgement is output and/or a standard setting and/or a predetermined initial state is set according to the method.

According to a further aspect, an imaging apparatus is disclosed. The imaging apparatus has an imaging modality, which is configured to generate a first image at a first capture time, which image represents an object to be depicted, and to generate a second image at a second capture time, which is after the first capture time, which image represents the object to be depicted. The imaging apparatus has at least one computing unit, which is configured to generate a further first image on the basis of the first image using a predefined model relating to a development over time of a contrast agent present in the object to be depicted when generating the first image, which further image takes into account the development over time of the contrast agent from the first capture time through to the second capture time. The at least one computing unit is configured to generate a further second image as a function of the second image and the further first image, in which image an effect of the contrast agent on the second image is at least partially compensated.

The imaging modality may have one or more control unit(s), it being possible for the at least one computing unit to contain or partially contain the at least one control unit, or vice versa.

According to at least one embodiment of the imaging apparatus, the imaging modality is configured as an X-ray based imaging modality.

In other words, the imaging modality includes an X-ray source and an X-ray-sensitive sensor unit.

Further embodiments of the imaging apparatus follow directly from the various embodiments of the method, and vice versa. In particular, individual features and corresponding explanations as well as advantages in respect of the various embodiments relating to the method may be transferred analogously to corresponding embodiments of the imaging apparatus. In particular, the imaging apparatus is embodied or programmed for carrying out a method. In particular, the imaging apparatus carries out the method.

A computing unit may refer to a data processing device that includes a processing circuit. The computing unit may process data in order to carry out computing operations, therefore. These optionally also include operations in order to carry out indicated instances of access to a data structure, for example, a look-up table (LUT).

The computing unit may include one or more computer(s), one or more microcontroller(s) and/or one or more integrated circuit(s), for example one or more application-specific integrated circuit(s) (ASIC), one or more Field Programmable Gate Array(s) (FPGA), and/or one or more System(s) on a Chip (SoC). The computing unit may also include one or more processor(s), for example one or more microprocessor(s), one or more central processing unit(s) (CPU), one or more graphics processing unit(s) (GPU) and/or one or more signal processor(s), in particular one or more digital signal processor(s) (DSP). The computing unit may also include a physical or a virtual group of computers or other of said units.

In various exemplary embodiments, the computing unit includes one or more hardware and/or software interface(s) and/or one or more storage unit(s).

A storage unit may be configured as a volatile data memory, for example as a dynamic random access memory (DRAM) or static random access memory (SRAM), or as a non-volatile data memory, for example as a read-only memory (ROM), as a programmable read-only memory (PROM), as an erasable programmable read-only memory (EPROM), as an electrically erasable programmable read-only memory (EEPROM), as a flash memory or flash EEPROM, as a ferroelectric random access memory (FRAM), as a magneto-resistive random access memory (MRAM) or as a phase-change random access memory (PCRAM).

According to a further aspect, a computer program with commands is disclosed. When the computer program is executed by an imaging apparatus, in particular the at least one computing unit, the commands cause the imaging apparatus to carry out an imaging method.

According to a further aspect, a computer-readable storage medium is disclosed, which stores a computer program.

The computer program and the computer-readable storage medium may be perceived as corresponding computer program products with the commands.

Further features of the disclosure may be found in the claims, figures, and description of the figures. The features and combinations of features cited above in the description as well as the features and combinations of features cited below in the description of the figures and/or shown in the figures may be incorporated by the disclosure not only in the respectively disclosed combination but also in other combinations. In particular, embodiments and combinations of features which do not have all features of an originally worded claim may also be incorporated by the disclosure. Furthermore, embodiments and combinations of features which go beyond the combinations of features presented in the back references of the claims or deviate from them may also be incorporated by the disclosure.

The disclosure is now explained in more detail below using specific exemplary embodiments and associated schematic drawings. Identical or functionally identical elements may be provided with the same reference numerals in the figures. The description of identical or functionally identical elements is optionally not necessarily be repeated in respect of different figures.

DETAILED DESCRIPTION

Figure 1:
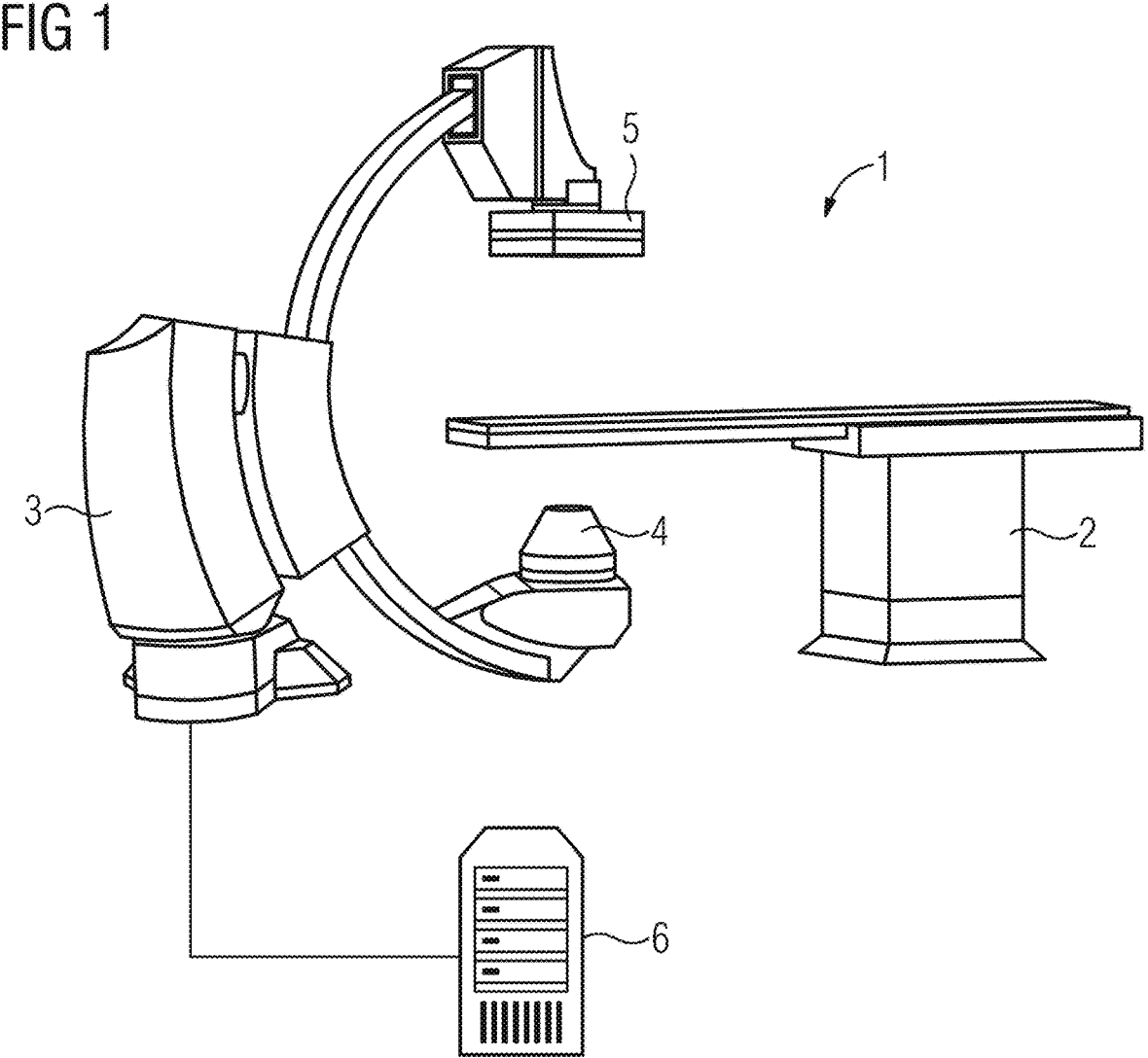
FIG. 1 depicts a schematic representation of an exemplary embodiment of an imaging apparatus.

FIG. 1 schematically shows an embodiment of an imaging apparatus 1 with an imaging modality 3, which may be configured, for example, as an X-ray based imaging modality with an X-ray source 4 and an X-ray sensor 5 and may optionally have a patient couch 2. The imaging apparatus 1 has a computing unit 6, which in different embodiments may also be representative of two of more computing units.

Figure 2:
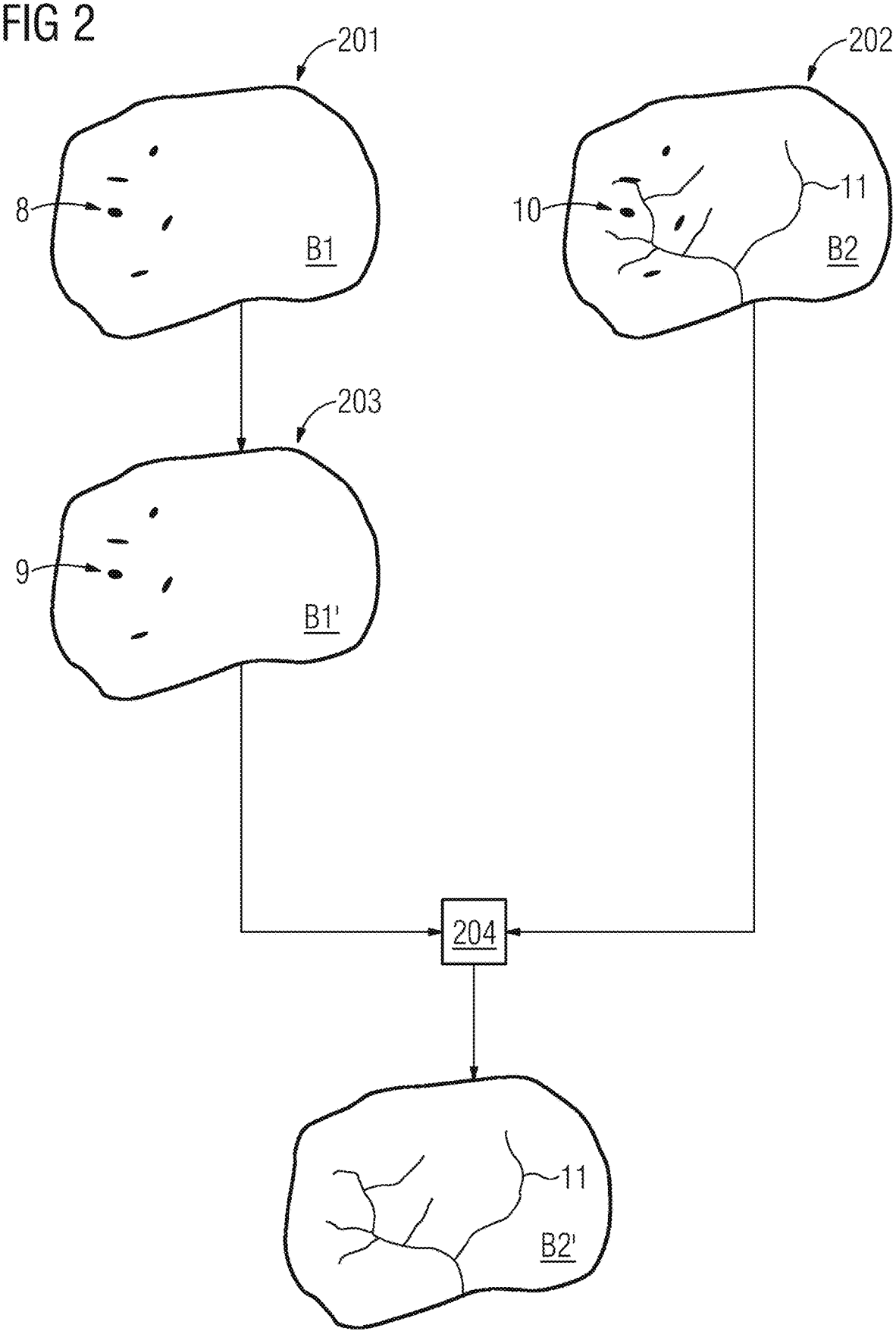
FIG. 2 depicts a schematic flowchart of an exemplary embodiment of an imaging method.

The imaging apparatus 1 is configured, in particular, to carry out an imaging method. FIG. 2 represents a flowchart for an imaging method of this kind in an exemplary embodiment.

In act 201, a first image B1 is generated at a first capture time by the imaging modality 3, wherein the first image B1 represents an object to be depicted, for example an organ.

In act 202, a second image B2 is generated at a second capture time, which is after the first capture time, by the imaging modality 3, wherein the second image B2 likewise represents the object to be depicted.

In the example of FIG. 2, the first image B1 depicts residues 8 of a contrast agent. The contrast agent may have been purposefully used for generating the first image B1 or it may be undesirable contrast agent residues from a preceding image generation. Between the first capture period and the second capture period, the contrast agent is subjected to a development over time, so the spatial distribution and/or concentration of the contrast agent in the object changes. The second image B2 accordingly depicts modified residues 10 of the contrast agent. The residues 8 and the modified residues 10 of the contrast agent differ due to the development over time of the spatial distribution and/or concentration of the contrast agent.

In addition, a further contrast agent was purposefully used in the present example of FIG. 2 for generating the second image B2, so the second image B2 shows a vascular structure 11 highlighted by the further contrast agent.

In act 203, the computing unit 3 generates a further first image BP on the basis of the first image B1 using a predefined model, which takes into account the development over time of the contrast agent, which results in the residues 8, 10, from the first capture time through to the second capture time. The first further image BP likewise shows modified residues 9 of the contrast agent accordingly. If the predefined model were to exactly reproduce the development over time of the contrast agent, the modified residues 9 in the first further image BP would be identical to the modified residues 10 in the second image B2. In any case, the modified residues 9 correspond at least approximately to the modified residues 10 in the second image B2.

In act 204, the computing unit 3 generates a further second image B2' on the basis of the further first image BP and the second image B2, in which image the effect of the contrast agent, which results in the residues 8, 10, is at least partially compensated. For example, the computing unit 3 may use the further first image B1' as a mask image for this purpose and subtract the further first image B1' from the second image B2. The vascular structure 11 is represented in the resulting further second image B2' as before therefore, but the residues 10 of the contrast agent are eliminated or partially eliminated.

Figure 3:
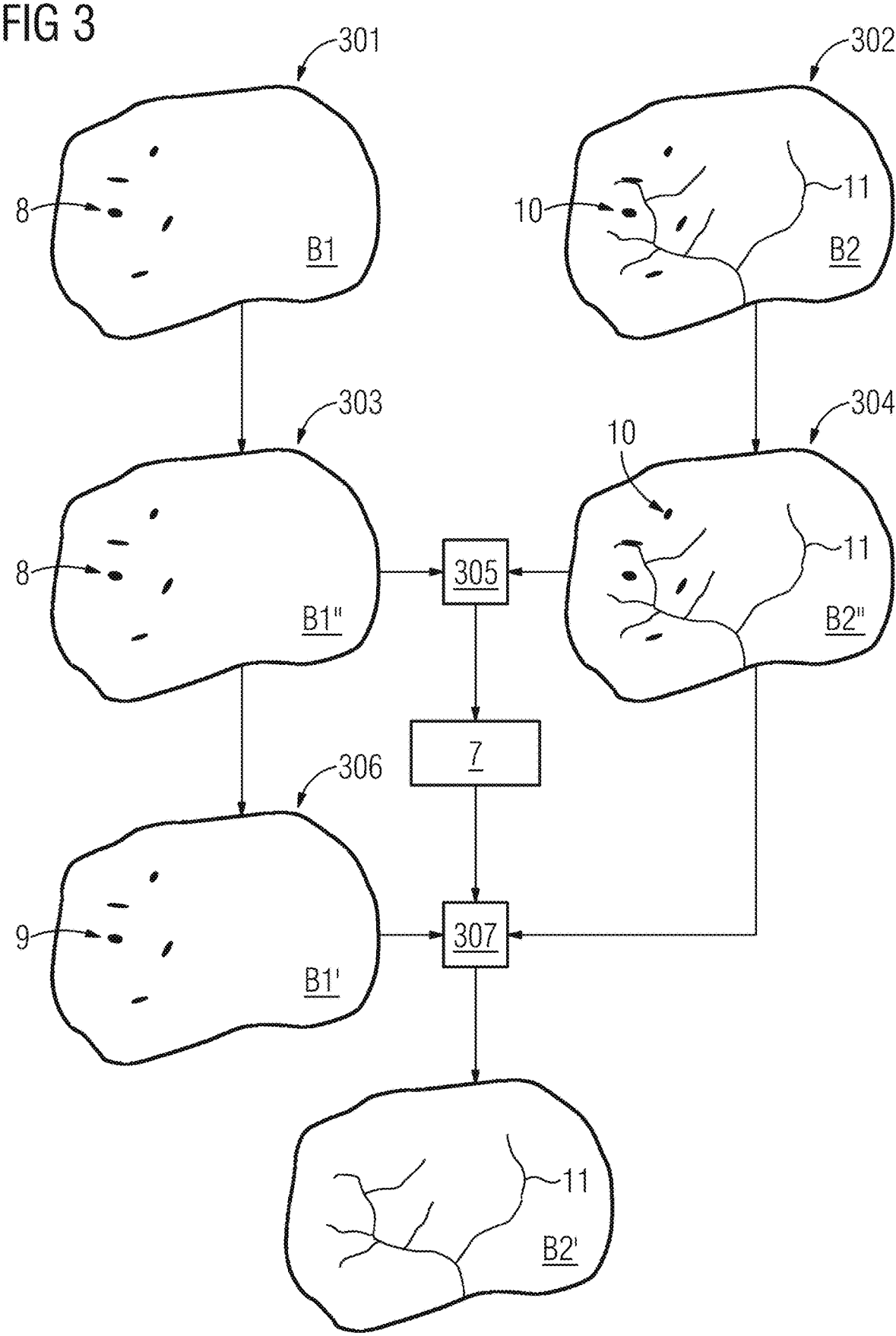
FIG. 3 depicts a flowchart of a further exemplary embodiment of an imaging method.

FIG. 3 represents a flowchart of a further exemplary embodiment of the imaging method.

In acts 301 and 302, the first image B1 and the second image B2 are generated, as explained in respect of FIG. 2. In the embodiment of FIG. 3, the first image B1 is segmented in act 303, so a segmented first image B1" results. Further, in act 304, the second image B2 is segmented, so a second segmented image B2" results.

Different image regions, also referred to as segments, are identified in the segmented first image B1", which regions also include a region which corresponds to the residues 8 of the contrast agent. Corresponding regions or segments have also been analogously identified in the second segmented image B2". Thus, for example, the segmented second image B2" may include regions which correspond to the residues 10 of the contrast agent, regions, which correspond to the vascular structure 11, in particular the further contrast agent therefore, etc. For example, both the first and the second segmented image B1", B2" may include regions or segments which correspond to static structures, for example skeletal structures. The respective position of these static structures may be adjusted by the computing unit 3 in act 305 in order to generate a transformation 7 for image registration.

The computing unit 3 also generates the further first image BP in act 306 on the basis of the segmented first image B1". For this, the computing unit 3 may purposefully apply the model to the regions or segments which specify the residues 8 of the contrast agent.

In act 307, the computing unit 3 generates the further second image B2' on the basis of the further first image BP and the segmented second image B2", for instance by way of subtraction as described above in respect of FIG. 2, in that the residues 10 of the contrast agent are partially or completely removed or compensated.

As described, in particular using the figures, the disclosure makes it possible to reduce the effect of undesirable contrast agent residues in an imaging method.

In some embodiments, the disclosure may also be applied to extract, (e.g., from X-ray photographs with a single type of radiation energy of from spectral computed tomography photographs or from cone beam computed tomography photographs), a distribution of contrast-enhancing materials, which may also be referred to as contrast agent, for instance of injected radiopaque embolization beads.

It is to be understood that the elements and features recited in the appended claims may be combined in different ways to produce new claims that likewise fall within the scope of the present disclosure. Thus, whereas the dependent claims appended below depend on only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. An imaging method comprising:
    generating a first image at a first capture time by an imaging apparatus, wherein the first image represents an object to be depicted, and wherein the first image comprises residues of a contrast agent used for the generating of the first image or from a preceding image generation;
    generating a second image at a second capture time that is after the first capture time, wherein the second image represents the object to be depicted, wherein further contrast agent is used in the generating of the second image, and wherein the second image depicts modified residues of the contrast agent as well as a vascular structure of the object highlighted by the further contrast agent;
    generating a further first image based on the first image using a predefined model relating to a development over time of the contrast agent present in the object to be depicted when generating the first image, wherein the further first image takes into account the development over time of the contrast agent from the first capture time through to the second capture time, wherein the further first image depicts modified residues of the contrast agent, and wherein the modified residues in the further first image correspond to the modified residues in the second image; and generating a further second image as a function of the second image and the further first image, wherein, in the further second image, the vascular structure of the object in the second image remains depicted while the modified residues of the contrast agent in the second image are at least partially eliminated.

2. The imaging method of claim 1, wherein the predefined model relates to a spatial distribution and/or concentration of the contrast agent as a function of time.

3. The imaging method of claim 1, further comprising:
generating a differential image by subtracting the further first image from the second image or the second image from the further first image,
wherein the further second image is generated as a function of the differential image or corresponds to the differential image.

4. The imaging method of claim 3, wherein the imaging method is embodied as a method for subtraction angiography,
wherein the further first image corresponds to a mask image of the subtraction angiography, and
wherein the second image corresponds to a vascular image of the subtraction angiography.

5. The imaging method of claim 1, wherein the first image is segmented to provide a segmented first image, and
wherein the further first image and/or the further second image is generated based on the segmented first image.

6. The imaging method of claim 5, wherein the generating of the further first image comprises modifying a first region of the segmented first image representing the contrast agent as a function of the predefined model according to the development over time of the contrast agent from the first capture time through to the second capture time.

7. The imaging method of claim 6, further comprising:
segmenting the second image;
determining a second region in the segmented second image, wherein the second region corresponds to a modified first region of the segmented first image; and
removing or partially removing the second region from the segmented second image to generate the further second image.

8. The imaging method of claim 7, further comprising:
determining a further first region of the segmented first image, wherein the further first region corresponds to a stationary anatomical structure;
determining a further second region of the segmented second image, wherein the further second region corresponds to the stationary anatomical structure;
determining a transformation for image registration as a function of the further first region and the further second region; and
generating the further second image as a function of the transformation.

9. The imaging method of claim 1, wherein the imaging method is embodied as a method for X-ray based angiography.

10. An imaging apparatus comprising:
an imaging modality configured to:
generate a first image at a first capture time, wherein the first image represents an object to be depicted, and wherein the first image comprises residues of a contrast agent used for the generation of the first image or from a preceding image generation; and
generate a second image at second capture time that is after the first capture time, wherein the second image represents the object to be depicted, wherein further contrast agent is used in the generation of the second image, and wherein the second image depicts modified residues of the contrast agent as well as a vascular structure of the object highlighted by the further contrast agent; and
at least one processor configured to:
generate a further first image based on the first image using a predefined model relating to a development over time of the contrast agent present in the object to be depicted when generating the first image, wherein the further first image takes into account the development over time of the contrast agent from the first capture time through to the second capture time, wherein the further first image depicts modified residues of the contrast agent, and wherein the modified residues in the further first image correspond to the modified residues in the second image; and
generate a further second image as a function of the second image and the further first image, wherein, in the further second image, the vascular structure of the object in the second image remains depicted while the modified residues of the contrast agent in the second image are at least partially eliminated.

11. The imaging apparatus of claim 10, wherein the imaging modality is embodied as an X-ray based imaging modality.

12. A non-transitory computer program product with commands, which when executed by an imaging apparatus comprising an imaging modality and at least one processor, cause the imaging apparatus to:
generate a first image at a first capture time, wherein the first image represents an object to be depicted, and wherein the first image comprises residues of a contrast agent used for the generation of the first image or from a preceding image generation;
generate a second image at a second capture time that is after the first capture time, wherein the second image represents the object to be depicted, wherein further contrast agent is used in the generation of the second image, and wherein the second image depicts modified residues of the contrast agent as well as a vascular structure of the object highlighted by the further contrast agent;
generate a further first image based on the first image using a predefined model relating to a development over time of the contrast agent present in the object to be depicted when generating the first image, wherein the further first image takes into account the development over time of the contrast agent from the first capture time through to the second capture time, wherein the further first image depicts modified residues of the contrast agent, and wherein the modified residues in the further first image correspond to the modified residues in the second image; and
generate a further second image as a function of the second image and the further first image, wherein, in the further second image, the vascular structure of the object in the second image remains depicted while the modified residues of the contrast agent in the second image are at least partially eliminated.

* * * * *